(12) United States Patent
Cohen et al.

(10) Patent No.: US 10,905,672 B2
(45) Date of Patent: Feb. 2, 2021

(54) COMBINATION OF BACLOFEN, ACAMPROSATE AND MEDIUM CHAIN TRIGLYCERIDES FOR THE TREATMENT OF NEUROLOGICAL DISORDERS

(71) Applicant: PHARNEXT, Issy les Moulineaux (FR)

(72) Inventors: Daniel Cohen, Saint Cloud (FR); Ilya Chumakov, Vaux-le-Penil (FR); Serguei Nabirochkin, Chatenay-Malabry (FR); Rodolphe Hajj, Saint Germain en Laye (FR)

(73) Assignee: PHARNEXT, Issy les Moulineaux (FR)

( * ) Notice: Subject to any disclaimer, the term of this patent is extended or adjusted under 35 U.S.C. 154(b) by 560 days.

(21) Appl. No.: 15/117,774

(22) PCT Filed: Feb. 10, 2015

(86) PCT No.: PCT/EP2015/052694
§ 371 (c)(1),
(2) Date: Aug. 10, 2016

(87) PCT Pub. No.: WO2015/121218
PCT Pub. Date: Aug. 20, 2015

(65) Prior Publication Data
US 2016/0354335 A1 Dec. 8, 2016

Related U.S. Application Data

(60) Provisional application No. 61/938,340, filed on Feb. 11, 2014.

(51) Int. Cl.
| | | |
|---|---|---|
| A61K 31/23 | (2006.01) | |
| A61K 31/185 | (2006.01) | |
| A61K 31/197 | (2006.01) | |
| A61K 31/20 | (2006.01) | |
| A61K 36/185 | (2006.01) | |
| A61P 25/28 | (2006.01) | |

(52) U.S. Cl.
CPC ............ *A61K 31/23* (2013.01); *A61K 31/185* (2013.01); *A61K 31/197* (2013.01); *A61K 31/20* (2013.01); *A61K 36/185* (2013.01); *A61P 25/28* (2018.01)

(58) Field of Classification Search
CPC ...................................................... A61K 31/23
USPC ......................................................... 514/456
See application file for complete search history.

(56) References Cited

U.S. PATENT DOCUMENTS

| | | |
|---|---|---|
| 8,552,041 B2 | 10/2013 | Cohen et al. |
| 8,716,269 B2 | 5/2014 | Cohen et al. |
| 8,741,886 B2 | 6/2014 | Cohen et al. |
| 8,809,302 B2 | 8/2014 | Cohen et al. |
| 8,865,769 B2 | 10/2014 | Cohen et al. |
| 8,992,891 B2 | 3/2015 | Cohen et al. |
| 9,144,558 B2 | 9/2015 | Cohen et al. |
| 9,241,933 B2 | 1/2016 | Cohen et al. |
| 9,248,111 B2 | 2/2016 | Cohen et al. |
| 9,387,206 B2 | 7/2016 | Cohen et al. |
| 9,393,241 B2 | 7/2016 | Cohen et al. |
| 9,427,436 B1 | 8/2016 | Cohen et al. |
| 9,545,389 B2 | 1/2017 | Cohen et al. |
| 9,566,275 B2 | 2/2017 | Cohen et al. |
| 9,597,297 B2 | 3/2017 | Cohen et al. |
| 9,636,316 B2 | 5/2017 | Cohen et al. |
| 9,700,036 B1 | 7/2017 | Chatelain et al. |
| 9,700,037 B1 | 7/2017 | Chatelain et al. |
| 9,820,978 B2 | 11/2017 | Cohen et al. |
| 9,867,837 B2 | 1/2018 | Cohen et al. |
| 9,931,326 B2 | 4/2018 | Cohen et al. |
| 10,004,744 B2 | 6/2018 | Cohen et al. |
| 10,010,515 B2 | 7/2018 | Cohen et al. |
| 10,045,971 B2 | 8/2018 | Cohen et al. |
| 10,342,768 B2 | 7/2019 | Cohen et al. |
| 10,342,784 B2 | 7/2019 | Cohen et al. |

(Continued)

FOREIGN PATENT DOCUMENTS

| | | |
|---|---|---|
| WO | WO 2009/005519 | 1/2009 |
| WO | WO 2011/082111 | 7/2011 |

(Continued)

OTHER PUBLICATIONS

Graham et al., Composition of seed oils in some Latin American Cuphea (Lythraceae), 1992, Industrial Crops and Products, vol. 1, pp. 31-34. (Year: 1992).*
Written Opinion in International Application No. PCT/EP2015/052694, dated Apr. 22, 2015, pp. 1-7.
Bliss, "The Toxicity of Poisons Applied Jointly," Annals of Applied Biology, 26(3):585-615 (1939).

*Primary Examiner* — Kortney L. Klinkel
*Assistant Examiner* — Tori Strong
(74) *Attorney, Agent, or Firm* — Browdy and Neimark, PLLC

(57) ABSTRACT

The present invention relates to combinations and methods for the treatment of neurological disorders related to amyloid beta toxicity and/or neuronal death and/or glucose-impaired neuronal metabolism. More specifically, the present invention relates to novel combinatorial therapies of Alzheimer's disease, Alzheimer's disease-related disorders, frontotemporal dementia, Parkinson's disease, Lewy body dementia, Huntington's disease, peripheral neuropathies, alcoholism or alcohol withdrawal, neurological manifestations of drug abuse or drug abuse withdrawal, amyotrophic lateral sclerosis, multiple sclerosis, spinal cord injury, epilepsy, traumatic brain injury or brain ischemic events based on baclofen, acamprosate and at least one medium chain triglyceride.

15 Claims, 2 Drawing Sheets

(56) References Cited

U.S. PATENT DOCUMENTS

| | | |
|---|---|---|
| 10,434,109 B2 | 10/2019 | Cohen et al. |
| 2002/0006959 A1* | 1/2002 | Henderson ............ A61K 31/12 514/552 |
| 2010/0310641 A1 | 12/2010 | Cohen et al. |
| 2011/0201558 A1 | 8/2011 | Roe et al. |
| 2011/0269764 A1 | 11/2011 | Cohen et al. |
| 2012/0040940 A1 | 2/2012 | Cohen et al. |
| 2012/0058992 A1 | 3/2012 | Cohen et al. |
| 2012/0071483 A1 | 3/2012 | Cohen et al. |
| 2012/0088744 A1 | 4/2012 | Cohen et al. |
| 2012/0270836 A1 | 10/2012 | Cohen et al. |
| 2013/0085122 A1* | 4/2013 | Cohen .................. A61K 31/137 514/171 |
| 2013/0090307 A1 | 4/2013 | Cohen et al. |
| 2014/0038927 A1 | 2/2014 | Cohen et al. |
| 2014/0080873 A1 | 3/2014 | Cohen et al. |
| 2014/0178463 A1 | 6/2014 | Cohen et al. |
| 2014/0235599 A1 | 8/2014 | Cohen et al. |
| 2014/0357648 A1 | 12/2014 | Cohen et al. |
| 2014/0371229 A1 | 12/2014 | Cohen et al. |
| 2014/0371277 A1 | 12/2014 | Cohen et al. |
| 2014/0378440 A1 | 12/2014 | Cohen et al. |
| 2015/0157626 A1 | 6/2015 | Cohen et al. |
| 2015/0224092 A1 | 8/2015 | Cohen et al. |
| 2015/0231123 A1 | 8/2015 | Cohen et al. |
| 2015/0238452 A1 | 8/2015 | Cohen et al. |
| 2015/0246044 A1 | 9/2015 | Cohen et al. |
| 2015/0301069 A1 | 10/2015 | Cohen et al. |
| 2015/0374647 A1 | 12/2015 | Cohen et al. |
| 2016/0000736 A1 | 1/2016 | Cohen et al. |
| 2016/0113867 A1 | 4/2016 | Cohen et al. |
| 2016/0136136 A1 | 5/2016 | Cohen et al. |
| 2016/0136143 A1 | 5/2016 | Cohen et al. |
| 2016/0193163 A1 | 7/2016 | Cohen et al. |
| 2016/0206603 A1 | 7/2016 | Cohen et al. |
| 2016/0235693 A1 | 8/2016 | Cohen et al. |
| 2016/0263104 A1 | 9/2016 | Cohen et al. |
| 2016/0354335 A1 | 12/2016 | Cohen et al. |
| 2016/0354362 A1 | 12/2016 | Cohen et al. |
| 2017/0049777 A1 | 2/2017 | Cohen et al. |
| 2017/0165256 A1 | 6/2017 | Cohen et al. |
| 2017/0231958 A1 | 8/2017 | Cohen et al. |
| 2018/0125867 A1 | 5/2018 | Cohen et al. |
| 2018/0263989 A1 | 9/2018 | Cohen et al. |
| 2019/0175568 A1 | 7/2019 | Cohen et al. |

FOREIGN PATENT DOCUMENTS

| | | |
|---|---|---|
| WO | 2012/117073 A2 | 9/2012 |
| WO | 2012/117075 A2 | 9/2012 |
| WO | 2012/117076 A2 | 9/2012 |
| WO | 2013/127917 A1 | 9/2013 |
| WO | 2013/127918 A1 | 9/2013 |
| WO | 2014/037416 A2 | 3/2014 |
| WO | 2015/028659 A1 | 3/2015 |
| WO | 2016/030522 A1 | 3/2016 |

* cited by examiner

COMBINATION OF BACLOFEN, ACAMPROSATE AND MEDIUM CHAIN TRIGLYCERIDES FOR THE TREATMENT OF NEUROLOGICAL DISORDERS

CROSS-REFERENCE TO RELATED APPLICATION

This application is the U.S. national stage application of International Patent Application No. PCT/EP2015/052694, filed Feb. 10, 2015.

FIELD OF THE INVENTION

The present invention relates to new combinations and methods for the treatment of neurological diseases and disorders. More specifically, the present invention relates to novel combinatorial therapies of neurological disorders, based on baclofen, acamprosate and medium chain mono-, di- or triglyceride(s) combinations.

BACKGROUND OF THE INVENTION

Alzheimer's disease (AD) is the prototypical cortical dementia, characterized by memory deficit together with dysphasia (language disorder in which there is an impairment of speech and comprehension of speech), dyspraxia (inability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved [1-4].

Incidence of AD increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis [5]. United Nations population projections estimate that the number of people older than 80 years will approach 370 million by the year 2050. Currently, it is estimated that 50% of people older than 85 years are afflicted with AD. Therefore, more than 100 million people worldwide will suffer from dementia in 50 years. The vast number of people requiring constant care and other services will severely affect medical, monetary and human resources [6].

Memory impairment is the early feature of the disease and involves episodic memory (memory for day-to-day events). Semantic memory (memory for verbal and visual meanings) is involved later in the disease. In contrast, working memory (short-term memory involving structures and processes used for temporarily storing and manipulating information) and procedural memory (unconscious memory that is long-term memory of skills and procedures) are preserved until late. As the disease progresses, the additional features of language impairment, visual perceptual and spatial deficits, agnosias and apraxias emerge.

The classic picture of AD is sufficiently characteristic to allow identification in approximately 80% of cases [7]. Nevertheless, clinical heterogeneity occurs which is important for clinical management and also provides further implication of specific medication treatments for functionally different forms [8].

The pathological hallmark of AD includes amyloid plaques containing beta-amyloid (Abeta), neurofibrillary tangles containing Tau and neuronal and synaptic dysfunction and loss [9-11]. For the last decade, two major hypotheses of the cause of AD have been proposed: the "amyloid cascade hypothesis", which states that the neurodegenerative process is a series of events triggered by the abnormal processing of the Amyloid Precursor Protein (APP) [12], and the "neuronal cytoskeletal degeneration hypothesis" [13], which proposes that cytoskeletal changes are the triggering events. The most widely accepted theory explaining AD progression remains the amyloid cascade hypothesis [14-16] and AD researchers have mainly focused on determining the mechanisms underlying the toxicity associated with Abeta proteins. Microvascular permeability and remodeling, aberrant angiogenesis and blood-brain barrier breakdown have been identified as key events contributing to the APP toxicity in the amyloid cascade [17]. On the contrary, Tau protein has received much less attention from the pharmaceutical industry than amyloid, because of both fundamental and practical concerns. Moreover, synaptic density change is the pathological lesion that better correlates with cognitive impairment than the two others. Studies have revealed that the amyloid pathology appears to progress in a neurotransmitter-specific manner, where the cholinergic terminals appear most vulnerable, followed by the glutamatergic terminals and finally by the GABAergic terminals [11]. Glutamate is the most abundant excitatory neurotransmitter in the mammalian nervous system. Under pathological conditions, its abnormal accumulation in the synaptic cleft leads to glutamate receptor overactivation [18], which results in pathological processes and finally in neuronal cell death. This process, named excitotoxicity, is commonly observed in neuronal tissues during acute and chronic neurological disorders.

Another principal functional hallmark of AD is profound generalized decline of energy metabolism characterized by mitochondrial dysfunction and development of an insulin resistance state, leading to reduced glucose uptake and, finally, synapses collapsing. An impaired brain metabolism is often suggested as a major etiological cause of cognitive decline in age-related dementias [28,29] and, in the case of AD, might precede, accompany or even provoke Abeta plaque deposition which, in a vicious cycle mechanism, could further inhibit glucose uptake [30].

Up to now, two kinds of medication, accounting for only five drugs approved in most countries, are used for improving or slowing down symptoms of AD, which lay on some acetylcholinesterase modulators and a blocker of NMDA glutamate receptors (NMDAR) [19-21].

Acetylcholinesterase inhibitors such as donepezil, rivastigmine, tacrine and galantamine are currently available in the market and are efficient at symptomatic relief with beneficial effects on cognitive, functional and behavioral symptoms (Aliabadi [22]).

NMDAR antagonists that target various sites of this receptor have been tested to counteract excitotoxicity. Uncompetitive NMDAR antagonists target the ion channel pores, thus reducing calcium entry into postsynaptic neurons. Only one of them, namely memantine, reached approval status for moderate to severe AD. This molecule is, however, of limited benefit to most AD patients, because it has only modest symptomatic effects and further has shown no significant effects in mild Alzheimer's disease [23,24]. Furthermore many other NMDAR antagonists have failed in advanced clinical trials for several neurodegenerative disorders [20,25,26]. Another approach in limiting excitotoxicity consists of inhibiting the presynaptic release of glutamate.

WO2009/133128, WO2009/133141, WO2009/133142, WO2011/054759, and WO2012/117076 disclose drug combinations suitable for use in the treatment of AD. WO2012/117076 particularly discloses the therapeutic efficacy of baclofen-acamprosate combinations in AD, including for the protection of glutamate toxicity and/or Abeta toxicity.

Despite active research in this area, there is still a need for alternative or improved, efficient therapies for neurological disorders and, in particular, neurological disorders which are related to glutamate and/or Abeta toxicity and/or impaired glucose metabolism in neuronal cells.

SUMMARY OF INVENTION

The present invention provides new therapeutic methods and compositions suitable for treating neurological disorders, particularly associated with neuronal cell death and cognitive decline. More particularly, the invention relates to compositions comprising baclofen, acamprosate, and at least one medium chain mono-, di- or triglyceride, as well as the use thereof for treating neurological disorders related to glutamate excitotoxicity and/or amyloid beta (Abeta) toxicity and/or impaired glucose brain metabolism.

The invention stems, inter alia, from the unexpected discovery, by the inventors, that the combination of baclofen, acamprosate and at least one medium chain mono-, di- or triglyceride provides substantial and unexpected benefit to patients with Alzheimer's disease (AD). In particular, the inventors have surprisingly discovered that such combinations provide substantial and unexpected improvement of cognitive function in in vivo AD models, resulting from a strong protection of neuronal cells.

Thus, the combination of baclofen, acamprosate and at least one medium chain mono-, di- or triglyceride constitutes an efficient treatment for patients suffering from, predisposed to, or suspected to suffer from neurological disorders.

An object of this invention therefore relates to compositions comprising (a combination of) baclofen and acamprosate and at least one medium chain mono-, di- or triglyceride, or a mixture thereof, preferably baclofen, acamprosate and at least one medium chain triglyceride (MCT).

In a particular embodiment, the medium chain mono-, di- or triglyceride has the formula:

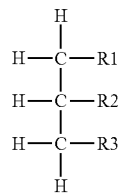

wherein R1, R2 and R3 are each independently a medium chain fatty acid (C6-C12) or a hydroxyl group, at least one of R1, R2 and R3 being a medium chain fatty acid (C6-C12).

In a more particular embodiment, R1, R2 and R3 are medium chain fatty acids (triglycerides); even more preferably R1, R2 and R3 are the same medium chain fatty acid.

The medium chain fatty acid may be selected from any fatty acid having from 6 to 12 carbon atoms such as, more preferably, caproic acid (C6), caprylic acid (C8), capric acid (C10) and/or lauric acid (C12). In this regard, preferred MCTs for use in the invention are caproic triglyceride, caprylic triglyceride, capric triglyceride and lauric triglyceride.

As will be further disclosed in the present application, the compounds in the compositions or combinations of the invention may be formulated separately or together. Also, they may be administered simultaneously, separately, sequentially and/or repeatedly to a subject.

The compositions of the invention typically further comprise one or several pharmaceutically acceptable excipients or carriers. Also, the compounds as used in the present invention may be in the form of a salt, hydrate, ester, ether, acid, amide, racemate, isomer, enantiomerically pure composition or conjugates. They may also be in the form of sustained-release formulations. Prodrugs or derivatives of the compounds may be used as well.

In a preferred embodiment, the compound is used as such or in the form a salt, hydrate, ester, ether or sustained-release form thereof. A particularly preferred salt for use in the present invention is acamprosate calcium.

In another preferred embodiment, a prodrug or derivative is used.

A further object of this invention is a method of preparing a pharmaceutical composition, the method comprising mixing baclofen, acamprosate, and the at least one medium chain mono-, di- or triglyceride in a pharmaceutically acceptable excipient or carrier.

Preferably, this method comprises mixing baclofen, acamprosate, and the at least one MCT in a pharmaceutically acceptable excipient or carrier.

A further object of the invention relates to compositions or combinations as defined above for use in the treatment of a neurological disorder, particularly Alzheimer's disease (AD), an AD-related disorder, frontotemporal dementia (FTD), Parkinson's disease (PD), Lewy body dementia, Huntington's disease (HD), amyotrophic lateral sclerosis (ALS), multiple sclerosis (MS), peripheral neuropathies, alcoholism or alcohol withdrawal, neurological manifestations of drug abuse or drug abuse withdrawal, spinal cord injury (SCI), epilepsy, traumatic brain injury or a brain ischemic event.

Another object of this invention relates to a method for treating a neurological disorder in a mammalian subject in need thereof, preferably a human subject in need thereof, the method comprising administering to said subject an effective amount of a composition or combination as defined above.

A further object of this invention relates to a method for treating AD or an AD-related disorder in a mammalian subject in need thereof, preferably a human subject in need thereof, the method comprising administering to said subject an effective amount of a composition or combination as defined above.

A preferred object of this invention relates to a method for treating a neurological disorder in a mammalian subject in need thereof, preferably a human subject in need thereof, the method comprising simultaneously, separately or sequentially administering to said subject an effective amount of baclofen, acamprosate and at least one medium chain mono-, di- or triglyceride.

More preferably, this method comprises simultaneously, separately or sequentially administering to said subject an effective amount of baclofen, acamprosate and at least one MCT.

A more preferred object of this invention relates to a method for treating AD or an AD-related disorder in a mammalian subject in need thereof, preferably a human subject in need thereof, the method comprising simultaneously, separately or sequentially administering to said subject an effective amount of baclofen, acamprosate and at least one medium chain mono-, di- or triglyceride.

Preferably, the method comprises simultaneously, separately or sequentially administering to said subject an effective amount of baclofen, acamprosate and at least one MCT.

More preferably, the method comprises simultaneously, separately or sequentially administering to said subject an effective amount of baclofen, acamprosate and at least one MCT compound selected from the group consisting of caprylic triglyceride, caproic triglyceride, capric triglyceride and lauric triglyceride, or a mixture thereof.

The invention may be used for treating a neurological disorder in any mammalian subject, preferably in any human subject, at any stage of the disease. As will be disclosed in the examples, the compositions of the invention are able to ameliorate the pathological condition of said subjects.

DETAILED DESCRIPTION OF THE INVENTION

Figure 1:
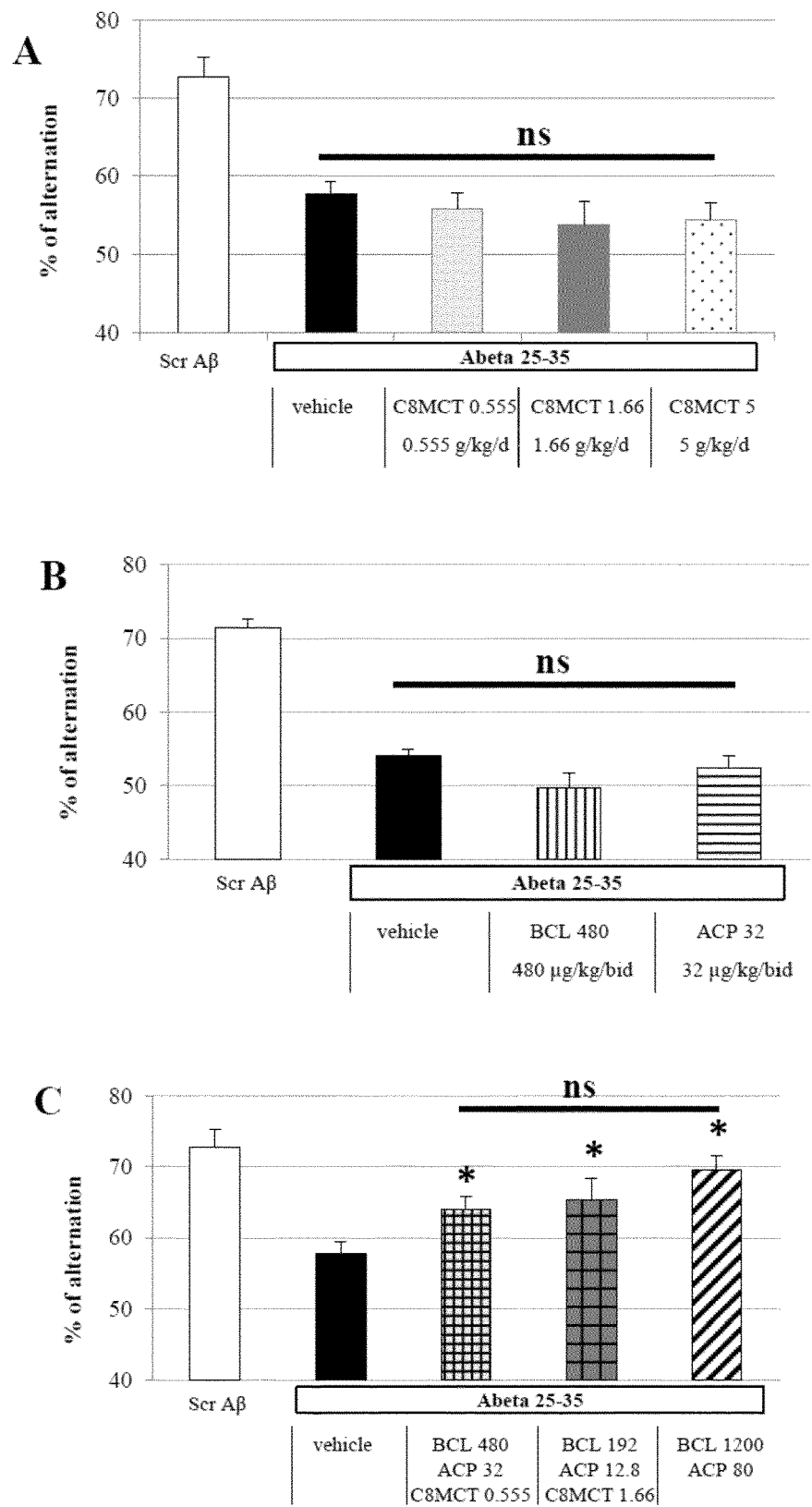
FIG. 1: Effects of acamprosate, baclofen and Medium Chain Triglyceride (MCT) combination therapy on behavior and cognitive performances of mice intoxicated by Abeta as defined by Y-maze spontaneous alternation test. The amyloid peptide Abeta 25-35 (black bar) produces a significant decrease in working memory compared to the control (scr scrambled Abeta 25-35, white bar) as measured by percentage of alternation. 1-A: C8 MCT administration does not improve working memory when compared to Abeta 25-35 intoxicated animals, whatever the doses used (C8MCT 0.555: 0.555 g/kg/d, light grey bar; C8MCT 1.66: 1.66 g/kg/d, dark grey bar; C8MCT 5: 5 g/kg/d, dotted bar). 1-B: Baclofen (BCL 480: 480 µg/kg/bid, vertically striped bar) or acamprosate (ACP 32: 32 µg/kg/bid, horizontally striped bar) alone does not improve working memory when compared to Abeta 25-35 intoxicated animals. 1-C: Working memory is significantly improved, compared to Abeta 25-35 intoxicated animals, by the use of compositions of the invention. The combination of BCL 480, ACP 32 and C8MCT 0.555 (light grey square-patterned bar) provides a statistically significant cognition improvement of 40% to the Abeta 25-35 intoxicated animals. The use of even lower concentrations of baclofen (BCL 192: 192 µg/kg/bid) and acamprosate (ACP 12.8: 12.8 µg/kg/bid) combined with a moderate concentration of C8 MCT (C8MCT 1.66, non-efficient dose when administered alone) also provides a statistically significant protection of 47% to Abeta 25-35 intoxicated animals (dark grey large square-patterned bar). The synergy between these compounds in combination has been statistically demonstrated ($P<0.005$); *: $P<0.05$, significantly different from Abeta 25-35 intoxication (type 3 Student's bilateral test); ns: no significant differences.

The present invention provides new methods and compositions for treating neurological disorders. The invention discloses novel active compound combinations which allow an effective correction of such diseases and may be used in any mammalian subject.

More particularly, the invention provides novel compositions comprising baclofen, acamprosate and at least one medium chain glyceride. As illustrated in the examples, the presence of a medium chain glyceride surprisingly increases the performances of the baclofen-acamprosate combination in vivo. The invention is therefore suited for treating any neurological disorders, particularly disorders which involve nerves and/or neuron injuries, beta-amyloid glutamate excitotoxicity and/or impaired glucose metabolism, such as neurodegenerative diseases.

An object of the invention therefore resides in a composition comprising:
  baclofen, or a pharmaceutically acceptable salt, hydrate, derivative, isomer, racemate, or prodrug thereof, of any chemical purity;
  acamprosate, or a pharmaceutically acceptable salt, hydrate, derivative, isomer, racemate, or prodrug thereof, of any chemical purity; and
  a medium chain mono-, di- or triglyceride.

Within the context of this invention, the designation of a specific drug or compound is meant to include not only the specifically named molecule, but also any pharmaceutically acceptable salt, hydrate, derivative, isomer, racemate, enantiomerically pure composition, conjugate, or prodrug thereof, of any chemical purity.

The term "prodrug" as used herein refers to any functional derivatives (or precursors) of a compound of the present invention, which, when administered to a biological system, generate said compound as a result of, e.g., spontaneous chemical reaction(s), enzyme-catalyzed chemical reaction(s), and/or metabolic chemical reaction(s). Prodrugs typically have the structure X-drug wherein X is an inert carrier moiety and drug is the active compound. Usually, the prodrug is devoid of activity or less active than the drug and the drug is released from the carrier in vivo. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups.

Prodrugs typically produced via the modification of these groups include, but are not limited to, esters, carbonates, carbamates, amides and phosphates. Specific technical guidance for the selection of suitable prodrugs is general common knowledge [33-37]. Furthermore, the preparation of prodrugs may be performed by conventional methods known by those skilled in the art. Methods which can be used to synthesize other prodrugs are described in numerous reviews on the subject [33-40]. For example, arbaclofen placarbil is listed in the ChemIDplus Advanced database (see Worldwide Web site: chem.sis.nlm.nih.gov/chemidplus/) and arbaclofen placarbil is a well-known prodrug of baclofen [41,42].

The term "derivative" of a compound includes any molecule that is functionally and/or structurally related to said compound, such as an acid, amide, ester, ether, acetylated variant, hydroxylated variant, or alkylated (C1-C6) variant of such a compound. The term derivative also includes structurally related compounds having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (see Worldwide Web site: pubchem.ncbi.nlm.nih.gov/search/) or DrugBank (see Worldwide Website: drugbank.ca/) [43]. In a more preferred embodiment, derivatives should have a Tanimoto similarity index greater than 0.4, preferably greater than 0.5, more preferably greater than 0.6, even more preferably greater than 0.7, with a parent drug. The Tanimoto similarity index is widely used to measure the degree of structural similarity between two molecules. Tanimoto similarity index can be computed by software such as the Small Molecule Subgraph Detector [44,45] available online (see Worldwide Website: ebi.ac.uk/thornton-srv/software/SMSD/). Preferred derivatives should be both structurally and functionally related to a parent compound, i.e., they should also retain at least part of the activity of the parent drug; more preferably, they should have a protective activity against Abeta toxicity.

The term "derivative" also includes metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, and that preferably has a protective activity against Abeta toxicity.

The term "salt" refers to a pharmaceutically acceptable and relatively non-toxic, inorganic or organic acid addition salt of a compound of the present invention. Pharmaceutical salt formation consists of pairing an acidic, basic or zwitterionic drug molecule with a counterion to create a salt version of the drug. A wide variety of chemical species can be used in neutralization reactions. Pharmaceutically acceptable salts of the invention thus include those obtained by reacting the main compound, functioning as a base, with an inorganic or organic acid to form a salt, for example, salts of acetic acid, nitric acid, tartaric acid, hydrochloric acid, sulfuric acid, phosphoric acid, methanesulfonic acid, camphorsulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalent, some may have, among other properties, increased solubility or bioavailability. Salt selection is now a common standard operation in the process of drug development as taught by Stahl and Wermuth in their handbook [46].

In a preferred embodiment, the designation of a compound is meant to designate the compound per se, as well as any pharmaceutically acceptable salt, hydrate, isomer, racemate, isomer, enantiomerically pure composition, ester or ether thereof.

In a more preferred embodiment, the designation of a compound is meant to designate the compound as specifically designated per se, as well as any pharmaceutically acceptable salt thereof.

In a particular embodiment, a sustained-release formulation of a compound is used.

Illustrative CAS numbers for baclofen and acamprosate and particular MCTs are provided in Table 1 below. Table 1 cites also, in a non-limiting way, common salts, racemates, isomers, enantiomerically pure compositions, prodrugs, metabolites or derivatives of the compounds according to the invention.

TABLE 1

| Drug | CAS Numbers | Class or Tanimoto similarity index |
| --- | --- | --- |
| Acamprosate and related compounds | | |
| Acamprosate | 77337-76-9; 77337-73-6 | NA |
| Homotaurine | 3687-18-1 | 0.73 |
| Ethyl dimethyl ammonio propane sulfonate | 160255-06-1 | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |
| 3-(p-chlorophenyl)-4-hydroxybutyric acid | 52977-95-4 | Metabolite |
| Arbaclofen placarbil | 847353-30-4 | Prodrug |
| MCT | | |
| Caprylic triglyceride | 538-23-8 | NA |
| Caproic triglyceride | 621-70-5 | NA |
| Capric triglyceride | 621-71-6 | NA |
| Lauric triglyceride | 538-24-9 | NA |

Specific examples of prodrugs of baclofen are given in Hanafi [47], particularly baclofen esters and baclofen ester carbamates, which are of particular interest for CNS targeting. Hence, such prodrugs are particularly suitable for compositions of this invention. Arbaclofen placarbil as mentioned before is also a well-known prodrug and may thus be used instead of baclofen in compositions of the invention. Other prodrugs of baclofen that can be used instead of baclofen in the compositions of the invention can be found in the following patent applications: WO2010/102071, U.S. 2009/197958, WO2009/096985, WO2009/061934, WO2008/086492, U.S. 2009/216037, WO2005/066122, U.S. 2011/021571, WO2003/077902 and WO2010/120370.

Useful prodrugs for acamprosate, such as pantoic acid ester neopentyl sulfonyl esters, neopentyl sulfonyl ester prodrugs or masked carboxylate neopentyl sulfonyl ester prodrugs of acamprosate, which can be used instead of acamprosate in the compositions of the invention, are notably listed in WO2009/033069, WO2009/033061, WO2009/033054 WO2009/052191, WO2009/033079, U.S. 2009/0099253, U.S. 2009/0069419, U.S. 2009/0082464, U.S. 2009/0082440 and U.S. 2009/0076147.

The term medium chain mono-, di- or triglyceride is intended to encompass any compound of formula I:

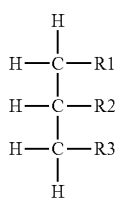

wherein R1, R2 and R3 are each independently a medium chain fatty acid (C6 to C12) or a hydroxyl group, at least one of R1, R2 and R3 being a medium chain fatty acid (C6-C12).

In a particular embodiment, two of R1, R2 and R3 are a medium chain fatty acid, which may be identical or different (diglyceride).

In a preferred embodiment, R1, R2 and R3 all represent a medium chain fatty acid (triglyceride), which may be identical or different, more preferably the same medium chain fatty acid.

The medium chain fatty acid may be any fatty acid having a carbon chain length comprising from 6 to 12 carbon atoms. Preferred examples of such fatty acids include caproic acid (C6), caprylic acid (C8), capric acid (C10) and lauric acid (C12).

In a preferred embodiment R1, R2 and R3 correspond to the same medium chain fatty acid selected from caproic acid (C6), caprylic acid (C8), capric acid (C10) and lauric acid (C12).

In a more preferred embodiment, R1, R2 and R3 are caprylic acid (C8).

The medium chain mono-, di- or triglyceride may comprise one molecular species or a mix of several medium chain mono-, di- or triglycerides as described above. In particular, the composition of the invention may comprise one MCT or a mixture of several MCTs, as described above.

The medium chain glyceride(s) may be synthetic, semi-synthetic and/or contained in or purified from natural sources.

MCTs may be produced by methods known per se in the art, such as chemical synthesis. Furthermore, medium chain mono-, di- or triglycerides are naturally present in coconut and palm kernel oils. These oils may be hydrolyzed using conventional methods to liberate their fatty acids from glycerol and the fatty acids then purified by fractional distillation. Pure MCT preparations can then be prepared through re-esterification of purified Medium Chain Fatty Acids (MCFA) on glycerol. Prior to esterification, different MCFAs can also be mixed in various ratios.

MCTs are also present in a wide variety of other vegetables, even if they are less exploited than coconut and palm kernel oils. For example, seeds of the *Cuphea* genus have been shown to produce oil composed of a diversity of MCFAs. Moreover, oils produced by certain species are almost constituted by one MCT. In *C. pulcherrima*, 94% of total seed oil composition is caprylic triglyceride and in *C. schumannii*, 94% is capric acid.

Hence, in a preferred embodiment, the compositions and methods of the invention utilize purified or semisynthetic MCTs. Alternatively, the invention also encompasses the use of impure triglyceride compositions, particularly vegetal products such as coconut, palm kernel, or *Cuphea*, and more particularly *C. pulcherrima* extracted oils, an extract thereof, or a mix thereof.

Preferred compositions of the invention comprise one of the following drug combinations, for combined, separate or sequential administration:

baclofen and acamprosate and caprylic triglyceride (C8),
baclofen and acamprosate and caproic triglyceride (C6),
baclofen and acamprosate and capric triglyceride (C10),
or
baclofen and acamprosate and lauric triglyceride (C12).

As discussed above, the drug combinations of the invention have a strong unexpected effect on several biological processes involved in neurological disorders. These new compositions can simultaneously, in a synergistic manner, attenuate Abeta toxicity, re-establish disturbed glutamate signaling and attenuate metabolic dysfunction in affected neurons.

In particular, the present application shows, in the Examples section, that combination therapies of the invention can substantially improve the condition of patients afflicted with neurological disorders. In particular, the inventors have surprisingly discovered that baclofen, acamprosate and MCT combinations have a strong unexpected effect on improving cognitive impairments observed in beta-amyloid intoxicated animals, and represent new therapeutic approaches for AD. Also, the examples show that in a combination therapy of the invention, baclofen, acamprosate and MCT efficiently correct cognitive impairments due to Abeta intoxication, even when used at low doses and/or dosages, thereby avoiding possible side effects.

These drug combinations therefore represent novel approaches for treating neurological disorders, such as AD and AD-related disorders, frontotemporal dementia, MS, ALS, PD, Lewy body dementia, HD, peripheral neuropathies, alcoholism or alcohol withdrawal, neurological manifestations of drug abuse or drug abuse withdrawal, SCI, epilepsy, traumatic brain injury or brain ischemic events.

The present invention therefore proposes a novel therapy of neurological disorders, based on baclofen, acamprosate and at least one medium chain mono-, di- or triglyceride composition. More particularly, the present invention proposes a novel therapy of AD and AD related disorders, frontotemporal dementia, MS, ALS, PD, Lewy body dementia, HD, peripheral neuropathies, alcoholism or alcohol withdrawal, neurological manifestations of drug abuse or drug abuse withdrawal, SCI, epilepsy, traumatic brain injury or brain ischemic events, based on baclofen, acamprosate and medium chain mono-, di- or triglyceride combinations.

In this regard, in a particular embodiment, the invention relates to a composition comprising baclofen and acamprosate and at least one medium chain mono-, di- or triglyceride for use in the treatment of AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events.

In a further embodiment, the invention relates to the use of baclofen, acamprosate and at least one MCT for the manufacture of a medicament for the treatment of AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events.

In a particular embodiment, the invention relates to the use of these combinations for treating AD or an AD-related disorder in a subject in need thereof.

In a particular embodiment, the invention relates to the use of these combinations for treating frontotemporal dementia, MS, PD, ALS, HD, peripheral neuropathies, alcoholism or alcohol withdrawal, neurological manifestations of drug abuse or drug abuse withdrawal, SCI, epilepsy, traumatic brain injury or brain ischemic events in a subject in need thereof.

As disclosed in the examples, composition therapies of the invention, comprising at least baclofen, acamprosate and an MCT, show in vivo a very efficient ability to correct memory and cognitive symptoms of neurological diseases in a model of AD. More particularly, these compositions efficiently improve in vivo several cognitive symptoms provoked by Abeta peptides. These combinations therefore represent novel approaches for treating neurological disorders, such as AD and AD-related disorders, frontotemporal dementia, MS, ALS, PD, Lewy body dementia, HD, peripheral neuropathies, alcoholism or alcohol withdrawal, neurological manifestations of drug abuse or drug abuse withdrawal, SCI, epilepsy, traumatic brain injury or brain ischemic events for treating cognitive symptoms associated with such disorders.

The Examples section further shows that the compositions of the invention are also efficient at synergistically protecting animals from cognitive impairment associated with neuronal death in neurological diseases.

Synergy can be proven in different ways, for instance, by calculating a combinatory index from dose-effect curves of each of the compounds alone and of their combinations [48-50] and/or using the factorial ANOVA test with treatments as factors, indicating whether an interaction between the factors is significant [51]. Synergy may be assessed by methods known by those skilled in the art.

As disclosed in the Examples section, combinatorial therapies of the invention provide substantial therapeutic and biological effects to improve AD or AD-related disorders in human subjects. They induce a strong improvement of memory and cognitive symptoms of neurological diseases as shown in behavioral performances in an in vivo model of AD. Their use is therefore of particular interest in subjects suffering from AD and AD-related disorders, more particularly in human subjects.

Moreover, the presented results also show that the above combination therapies have an important synergistic effect against cognitive impairment related to Abeta toxicity.

These compositions efficiently prevent the toxic effects of Abeta protein or peptide in an in vivo model and thus represent novel and potent methods for treating AD, AD-related disorders and other disorders which share some physiological features with AD.

An object of this invention thus also resides in a composition as defined above for treating a neurological disorder such as AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events.

More particularly, examples show that compositions of the invention are particularly efficient at protecting short-term memory and also long-term memory in vivo.

Consequently, an object of this invention is the use of baclofen, acamprosate and at least one medium chain mono-, di- or triglyceride for improving short-term memory and/or long-term memory in subjects suffering from AD, AD-related disorders, frontotemporal dementia, PD, Lewy body dementia, HD, ALS, MS, peripheral neuropathies, alcoholism or alcohol withdrawal, neurological manifestations of drug abuse or drug abuse withdrawal, SCI, epilepsy, traumatic brain injury or brain ischemic events.

As indicated previously, in a combination therapy of this invention, the compounds or drugs may be formulated together or separately, and administered together, separately or sequentially.

A further object of this invention resides in the use of a composition as defined above for the manufacture of a medicament for treating a neurological disorder such as AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events.

The invention further provides a method for treating a neurological disorder such as AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events, comprising administering to a subject in need thereof an effective amount of a composition as disclosed above.

A further object of the invention is a method of treating a neurological disorder such as AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events, the method comprising simultaneously, separately or sequentially administering to a subject in need thereof an effective amount of a composition as disclosed above.

In a preferred embodiment, the invention relates to a method of treating a neurological disorder such as AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events in a subject in need thereof, comprising administering simultaneously, separately or sequentially to the subject an effective amount of baclofen, acamprosate and at least one medium chain mono-, di- or triglyceride.

In a more preferred embodiment, the invention relates to a method of treating a neurological disorder such as AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events in a subject in need thereof, comprising administering simultaneously, separately or sequentially to the subject an effective amount of baclofen, acamprosate and at least one MCT.

Neurodegenerative disorders refer to diseases, such as Alzheimer's disease (AD) and AD-related disorders, frontotemporal dementia (FTD), amyotrophic lateral sclerosis (ALS), multiple sclerosis (MS), Parkinson's disease (PD), Lewy body dementia, Huntington's disease (HD), spinal cord injury (SCI), brain ischemic events, or epilepsy encompassing a progressive loss of function and death of neurons.

The invention is particularly suited for treating AD and AD-related disorders. In the context of this invention, the term "AD-related disorder" includes senile dementia of AD type (SDAT), vascular dementia, mild cognitive impairment (MCI) and age-associated memory impairment (AAMI).

As used herein, the term "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes protection against i) the toxicity caused by beta amyloid (Abeta), or a reduction or retardation of said toxicity, and/or ii) a protection against glutamate excitotoxicity, or a reduction or retardation of said toxicity, and/or iii) an improved energy metabolism of neurons in the treated subjects. The term treatment also designates an improvement of cognitive symptoms or a protection of neuronal cells.

The term "combination or combinatorial treating/therapy" designates a treatment wherein at least baclofen, acamprosate and the at least one medium chain mono-, di- or triglyceride are co-administered to a subject to cause a biological effect. In a combined therapy according to this invention, the at least three compounds may be administered together or separately, at the same time or sequentially. Also, the at least baclofen, acamprosate and at least one medium chain mono-, di- or triglyceride may be administered through different routes and protocols.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

In a particular embodiment, the method comprises mixing baclofen, acamprosate and at least one medium chain mono-, di- or triglyceride in an appropriate excipient or carrier. Preferably, the at least one medium chain mono-, di- or triglyceride is at least one MCT.

According to preferred embodiments of the invention, as indicated above, the compounds are used as such or in the form of a pharmaceutically acceptable salt, prodrug, derivative, or sustained/controlled-release formulation thereof.

Although very effective in vivo, depending on the subject or specific condition, the combination therapy of the invention may further be used in conjunction, association or combination with additional drugs or treatments beneficial to treating neurological conditions in the subjects.

Other therapies used in conjunction with drug(s) or drug(s) combination(s) according to the present invention may comprise one or more drug(s) that ameliorate symptoms of AD, AD-related disorders, frontotemporal dementia, MS, PD, Lewy body dementia, ALS, HD, peripheral neuropathies, alcoholism or alcohol withdrawal, neurological manifestations of drug abuse or drug abuse withdrawal, SCI, epilepsy, traumatic brain injury or brain ischemic events, or drug(s) that could be used for palliative treatment of these disorders. Thereby, illustrative therapies which can be used with combinations of the invention are tacrine (CAS: 321-64-2), donepezil (CAS: 120014-06-4), galantamine (CAS: 357-70-0; 1953-04-4), rivastigmine (CAS: 123441-03-2) or memantine (CAS: 19982-08-2) for AD and AD-related disorders, or lisuride (CAS: 140387-89-9, 1189731-50-7, 14611-52-0, 14611-51-9), rasagiline (CAS: 136236-51-6), tolcapone (CAS: 134308-13-7), entacapone (CAS: 130929-57-6), clozapine (CAS: 5786-21-0), desipramine (CAS: 50-47-5), citalopram (CAS: 59729-33-8), nortriptyline (CAS: 72-69-5), paroxetine (CAS: 61869-08-7), atomoxetine (CAS: 82248-59-7), venlafaxine (CAS: 93413-69-5), amantadine (CAS: 768-94-5), donepezil (CAS: 120014-06-4), rivastigmine (CAS: 123441-03-2), memantine (CAS: 19982-08-2), levodopa (CAS: 59-92-7), bromocriptine (CAS: 25614-03-3), cabergoline (CAS: 81409-90-7), pergolide (CAS: 66104-22-1), pramipexole (CAS: 104632-26-0), ropinirole (CAS: 91374-21-9), rotigotine (CAS: 99755-59-6, 92206-54-7), apomorphine (CAS: 58-00-4), carbidopa (CAS: 28860-95-9), benserazide (CAS: 322-35-0), selegiline (CAS: 14611-51-9), omigapil (CAS: 181296-84-4), CEP-1347 (CAS: 156177-65-0), isradipine (CAS: 75695-93-1) or DOPA (CAS: 59-92-7) for PD, or lithium or riluzole (CAS: 1744-22-5) for ALS, or levetiracetam (CAS: 102767-28-2), ezogabine (CAS: 150812-12-7), pregabalin (CAS: 148553-50-8), rufinamide (CAS: 106308-44-5), felbamate (CAS: 25451-15-4), carbamazepine (CAS: 298-46-4), valproate (CAS: 99-66-1), sodium valproate (CAS: 1069-66-5), lamotrigine (CAS: 84057-84-1), phenytoin (CAS: 57-41-0), oxcarbazepine (CAS: 28721-07-5), ethosuximide (CAS: 77-67-8, 39122-19-5, 39122-20-8), gabapentin (CAS: 60142-96-3), tiagabine (CAS: 115103-54-3), topiramate (CAS: 97240-79-4), vigabatrin (CAS: 60643-86-9), phenobarbital (CAS: 50-06-6), primidone (CAS: 125-33-7) or clonazepam (CAS: 1622-61-3) for epilepsy, or interferon beta-la (CAS: 145258-61-3), interferon beta-lb (CAS: 145155-23-3), mitoxantrone (CAS: 65271-80-9), natalizumab (CAS: 189261-10-7), fingolimod (CAS: 162359-55-9), natalizumab (CAS: 189261-10-7), teriflunomide (CAS: 108605-62-5), dimethyl fumarate (CAS: 624-49-7, 23057-98-9) or glatiramer (CAS: 28704-27-0; 147245-92-9) for MS.

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, the age and condition of the patient, and how the patient responds to the treatment. The dosage, frequency and mode of administration of each component of the combination can be controlled independently. For example, one compound may be administered orally while the second compound may be administered intramuscularly. Combination therapy may be given in on-and-off cycles that include rest periods so that the patient's body has a chance to recover from any as-yet unforeseen side effects. The compounds may also be formulated together such that one administration delivers all the drugs.

The administration of each compound of the combination may be by any suitable means that results in a concentration of the compound that, combined with the other component(s), is able to ameliorate the patient's condition and/or efficiently treat the disease or disorder.

While it is possible for the compounds of the combination to be administered as the pure chemicals, it is preferable to present them as a pharmaceutical composition, also referred to in this context as a pharmaceutical formulation. Possible compositions include those suitable for oral, rectal, topical (including transdermal, buccal and sublingual), or parenteral (including subcutaneous, intramuscular, intravenous and intradermal) administration.

More commonly, these pharmaceutical formulations are prescribed to the patient in "patient packs" containing a number of dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein described, in combination with packaging material suitable for said formulation. In such a patient pack the intended use of a formulation for the combination treatment can be inferred by instructions, facilities, provisions, adaptations and/or other means to help use the formulation most suitably for the treatment. Such measures make a patient pack specifically suitable and adapted for use for treatment with the combinations of the present invention.

The compound(s) may be contained, in any appropriate amount, in any suitable carrier substance. The compound(s) may be present in an amount of up to 99% by weight of the total weight of the composition. The composition may be provided in a dosage form that is suitable for the oral, parenteral (e.g., intravenous, intramuscular), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy [52] and the Encyclopedia of Pharmaceutical Technology [53]).

Pharmaceutical compositions according to the invention may be formulated to release the active compound(s) substantially immediately upon administration or at any predetermined time or time period after administration.

The sustained/controlled release formulations include: (i) formulations that create a substantially constant concentration of the compound within the body over an extended period of time; (ii) formulations that after a predetermined lag time create a substantially constant concentration of the compound within the body over an extended period of time; (iii) formulations that sustain compound action during a predetermined time period by maintaining a relatively constant, effective drug level in the body with concomitant minimization of undesirable side effects associated with fluctuations in the plasma level of the active drug substance; (iv) formulations that localize compound action by, e.g., spatial placement of a controlled release composition adjacent to or in the diseased tissue or organ; and (v) formulations that target compound action by using carriers or chemical derivatives to deliver the drug to a particular target cell type.

Administration of drugs in the form of a sustained/controlled-release formulation is especially preferred in cases in which the drug has: (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastrointestinal tract; or (iii) a very short biological half-life so that frequent dosing during a day is required in order to sustain the plasma level at a therapeutic level.

Any of a number of strategies can be pursued in order to obtain sustained/controlled release in which the rate of release outweighs the rate of metabolism of the compound in question. Controlled release may be obtained by appropriate selection of various formulation parameters and ingredients, including, e.g., various types of controlled-release compositions and coatings. Thus, the compound is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active compound substance in a predetermined pattern (e.g., in order to achieve a controlled release formulation) or it may be adapted not to release the active compound substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner to that described in the Encyclopedia of Pharmaceutical Technology [53].

Drugs/compounds may be mixed together in the tablet, or may be partitioned. For example, a first compound is contained on the inside of the tablet, and a second compound is on the outside, such that a substantial portion of the second compound is released prior to the release of the first compound.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance. Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, DL-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric contents for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents include, for example, sodium carboxymethylcellulose, methylcellulose, sodium alginate, and the like.

Parenteral Compositions

The pharmaceutical composition(s) may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well-known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active compound(s), the composition may include suitable parenterally acceptable carriers and/or excipients. The active compound(s) may be incorporated into microspheres, microcapsules, nanoparticles, liposomes, or the like for controlled release. The composition may include suspending, solubilizing, stabilizing, pH-adjusting, and/or dispersing agents.

The pharmaceutical compositions according to the invention may be in a form suitable for sterile injection. To prepare such a composition, the suitable active compound(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compound(s) is/are only sparingly or slightly soluble in water, a dissolution-enhancing or solubilizing agent can be added, or the solvent may include 10-60% w/w of propylene glycol or the like.

Controlled-release parenteral compositions may be in form of aqueous suspensions, microspheres, microcapsules, magnetic microspheres, oil solutions, oil suspensions, or emulsions. Alternatively, the active compound(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), and poly(2-hydroxyethyl-L-glutamnine). Biocompatible carriers that may be used when formulating a controlled-release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type) and rectal gelatin capsules (solutions or suspensions). In a typical suppository formulation, the active compound(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutically acceptable carriers and excipients, including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, and penetration enhancers may be parabens, such as methyl or propyl p-hydroxybenzoate, benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or, alternatively, plasters, pads, sponges, strips, or other forms of suitable flexible material.

Slow-Release Formulations

Any of the compounds of the combinatorial therapy of the invention may be used in slow-release formulations, and/or formulated with agents that modify tissue distribution or bioavailability. More particularly, when applicable, one or more compound(s) of the therapy of the invention are formulated with drug-eluting polymers, biomolecules, micelles, liposome-forming lipids, or oil-in-water emulsions, or pegylated or solid nanoparticles or microparticles for oral or parenteral or intrathecal administration, to modify tissue distribution or bioavailability. Specific examples of such formulating agents include PGA, PLGA, cyclodextrins, albumin or protein carriers, nano- and microparticles, liposomes, emulsions, and PEG.

Conjugates

In combination therapies of this invention, the compounds may be associated in pharmaceutical compositions in different ways. They may be mixed together as separate entities. They may be formulated separately. They may also be linked, covalently or non-covalently, with or without a linker. In a particular embodiment, at least two compounds are linked, preferably through a cleavable or non-cleavable linker.

Dosages and Duration of the Treatment

It will be appreciated that the drugs/compounds of the combination(s) may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help use the combination according to the invention.

Therapeutically effective amounts of the compounds in a combination of this invention include, e.g., amounts that are effective for reducing AD symptoms, halting or slowing the progression of the disease once it has become clinically manifested, or prevention or reduction of the risk of developing the disease.

Although the active drugs of the present invention may be administered in divided doses, for example two or three times daily, a single daily dose of each compound in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration is indicated in most cases.

The term "unit dosage form" refers to physically discrete units (such as capsules, tablets, loaded syringe cylinders, shaker cups, or ampoules) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, and the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds individually have little or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, ⅙, 1/7, ⅛, 1/9 or even more preferably 1/10 of therapeutic doses. In particular examples, doses as low as 1/20, 1/30, 1/50, 1/100, or even lower, of therapeutic doses are used.

At such sub-therapeutic dosages, the compounds would exhibit no side effects, while the combination(s) according to the invention are fully effective in treating AD.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of compounds for use in the invention are provided below:

Acamprosate between 0.1 and 1000 mg/day, preferably less than 400 mg/day, preferably less than 200 mg/day, more preferably less than 100 mg/day, even more preferably less than 50 mg/day, such dosages being particularly suitable for oral administration.

Baclofen between 0.01 and 150 mg/day, preferably less than 100 mg/day, more preferably less than 50 mg/day, even more preferably less than 25 mg/day, such dosages being particularly suitable for oral administration.

Caprylic triglyceride between 0.1 and 15 g/day, preferably less than 10 g/day by oral administration.

In the compositions of the invention, baclofen and acamprosate may be used in different ratios, e.g., at a weight ratio of acamprosate/baclofen comprised between 0.05 and 1000 (w/w), preferably between 0.05 and 100 (w/w), more preferably between 0.05 and 50 (w/w).

It will be understood that the amount of the compounds actually administered will be determined by a physician, in light of the relevant circumstances including the condition or conditions to be treated, the exact composition to be administered, the age, weight, and response of the patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

The care and husbandry of animals as well as the experimentations are performed according to the guidelines of the Committee for Research and Ethical Issues of the I.A.S.P. (1983).

Baclofen-Acamprosate and MCT Combination Therapies Prevent Toxicity of Human Abeta 25-35 In Vivo.

Animals

Male Swiss mice are used throughout the study. Animals are housed in plastic cages, with free access to laboratory chow and water, except during behavioral experiments, and kept in a regulated environment, under a 12 h light/dark cycle (light on at 8:00 a.m.). Experiments are carried out in a soundproof and air-regulated experimental room to which mice have been habituated at least 30 min before each experiment.

Combinatory Treatment

Drug(s) is/are administered daily by gavage (per os). The Abeta 25-35 peptide and scrambled Abeta 25-35 peptide (control) have been dissolved in sterile bidistilled water, and stored at −20° C. until use [54]. The Abeta peptides are then administered intracerebroventricularly (icy). In brief, each mouse is anesthetized lightly with ether, and a gauge stainless-steel needle is inserted unilaterally 1 mm to the right of the midline point equidistant from each eye, at an equal distance between the eyes and the ears and perpendicular to the plane of the skull. Peptides or vehicle are delivered gradually within approximately 3 s. Mice exhibit normal behavior within 1 min after injection. The administration site is checked by injecting Indian ink in preliminary experiments. Neither insertion of the needle nor injection of the vehicle has a significant influence on survival, behavioral responses or cognitive functions.

Drug(s) Treatment

On day −1, i.e., 24 h before the Abeta 25-35 peptide injection, drugs, candidate combinations, baclofen acamprosate mix, or the vehicle solution are administered per os by gavage twice daily (at 8:00 a.m. and 6:00 p.m.), and caprylic triglyceride is administered per os by gavage once daily (at 8:00 a.m.).

On day 0 (at 10:00 a.m.), mice are injected icy with Abeta 25-35 peptide or scrambled Abeta 25-35 peptide (control) in a final volume of 3 µL (3 mM).

Between day 0 and day 7, drugs, drug combinations or the vehicle solution are administered per os by gavage once or twice daily (at 8:00 a.m. for caprylic triglyceride or at 8:00 a.m. and 6:00 p.m. for baclofen and acamprosate). As a positive control, one animal group receives donepezil (reference compound—1 mg/kg/day) per os by gavage in a single injection (at 8:00 a.m.). Drugs are solubilized in water and freshly prepared just before each gavage administration.

On day 7, all animals are tested for spontaneous alternation performance in the Y-maze test, an index of spatial working memory (short-term memory).

On days 8 and 9, the contextual long-term memory of the animals is assessed using the step-through type passive avoidance procedure.

On day 9, animals are sacrificed. Blood samples (plasma) are collected for further analysis.

Tested doses of compounds are given in Table 2 below.

TABLE 2

| | R/S baclofen µg/kg/bid | Acamprosate µg/kg/bid | Caprylic triglyceride g/kg/d |
|---|---|---|---|
| Dose 1 | 192 | 12.8 | 0.555 |
| Dose 2 | 480 | 32 | 1.66 |
| Dose 3 | 1200 | 80 | 5 |

Dose 1 and dose 2 of caprylic triglyceride are respectively less than ⅙ and less than ½ of the usually prescribed dosage.

Combinations Enhance Behavioral and Cognitive Performances of Abeta 25-35 Intoxicated Animals.

Spontaneous Alternation Performances—Y Maze Test

On day 7, all animals are tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converges at an equal angle. Each mouse is placed at the end of one arm and allowed to move freely through the maze during an 8 min session. The series of arm entries, including possible returns into the same arm, are checked visually. An alternation is defined as entries into all three arms on consecutive occasions. The number of maximum alternations is therefore the total number of arm entries minus two and the percentage of alternation is calculated as (actual alternations/maximum alternations)×100. Parameters include the percentage of alternation (memory index) and total number of arm entries (exploration index). Animals that show an extreme behavior (alternation percentage <25% or >85% or number of arm entries <10) are discarded. Usually, this accounts for 0-5% of the animals. This test incidentally serves to analyze, at the behavioral level, the impact and the amnesic effect induced in mice by the Abeta 25-35 injection.

Passive Avoidance Test

The apparatus is a two-compartment (15×20×15 cm high) box with one compartment being illuminated with white polyvinylchloride walls and the other compartment darkened with black polyvinylchloride walls and a grid floor. A guillotine door separates each compartment. A 60 W lamp positioned 40 cm above the apparatus lights up the white compartment during the experiment. Scrambled footshocks (0.3 mA for 3 s) could be delivered to the grid floor using a shock generator scrambler (Lafayette Instruments, Lafayette, USA). The guillotine door is initially closed during the training session. Each mouse is placed into the white compartment. After 5 s, the door raises. When the mouse enters the darkened compartment and places all its paws on the grid floor, the door closes and the footshock is delivered for 3 s. The step-through latency, that is, the latency spent to enter the darkened compartment, and the number of vocalizations is recorded. The retention test, carried out 24 h after training, constitutes an index for long-term memory. Each mouse is placed again into the white compartment. After 5 s the door is raised, and the step-through latency and the escape latency, i.e., the time spent to return into the white compartment, are recorded up to 300 s.

Positive results are observed in behavioral and cognitive performances in the two tests for animals dosed with combinations of the invention.

Figure 2:
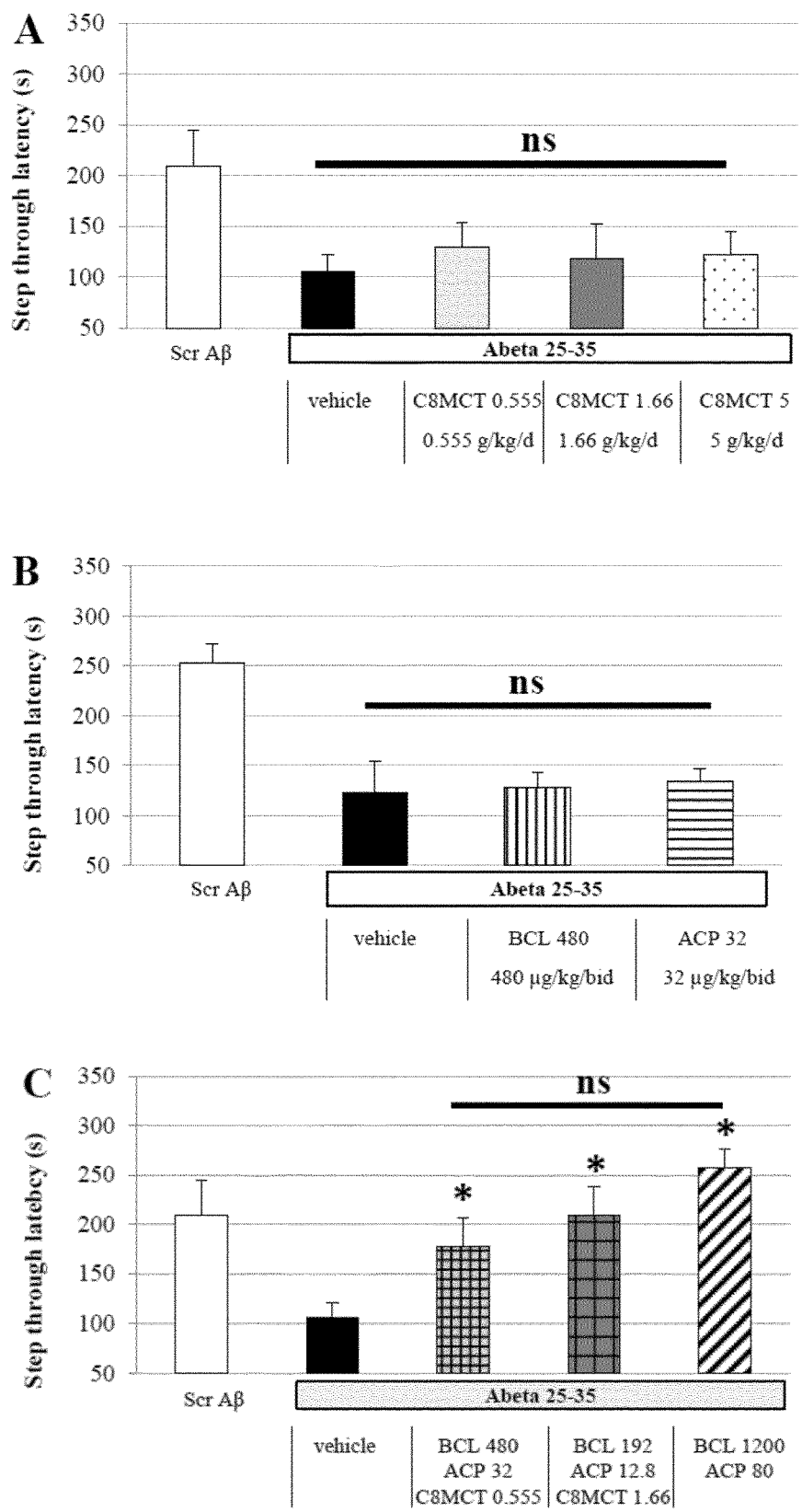
FIG. 2: Effect of baclofen, acamprosate and MCT combination therapy on memory defects provoked by Abeta in mice as defined by the passive avoidance test (step-through latency). The amyloid peptide Abeta 25-35 (black bar) produces a significant decrease in memory performances as measured by step-through latency compared to control (white bar). 2-A: C8 MCT administration does not provide any statistically significant effect on memory defects caused by Abeta, compared to Abeta 25-35 intoxicated animals, whatever the doses used (C8MCT 0.555, C8MCT 1.66 and C8MCT 5). 2-B: BCL 480 or ACP 32 monotherapy does not provide any improvement when compared to Abeta 25-35 intoxicated animals. 2-C: The memory defects provoked by Abeta are significantly reversed by the use of the drug combinations of the invention (BCL 480, ACP 32 and C8MCT 0.555, or BCL 192, ACP 12.8 and C8MCT 1.66). The synergy between the compounds has been statistically demonstrated ($P<0.001$); *: $P<0.05$, significantly different from Abeta 25-35 intoxication (type 3 Student's bilateral test); ns: no significant differences; cf. legend of FIG. 1.

The compositions of the invention induce a significant protective effect on behavioral and cognitive performances of Abeta 25-35 intoxicated animals, as shown in FIGS. 1 and 2.

In FIG. 1, the Abeta 25-35 intoxicated mice (black bar) exhibit a strongly impaired spatial working memory compared to controls (white bar). No significant effect is observed when caprylic triglyceride is used alone, whatever the doses used (FIG. 1-A: C8MCT 0.555: 0.555 g/kg/d, C8MCT 1.66: 1.66 g/kg/d, C8MCT 5: 5 g/kg/d). It should be noted that dose 3 (5 g/kg/d), converted into a human equivalent dose, is in the range of the prescribed dose in the medical food currently on the market.

No significant effect is achieved either with the use of baclofen (BCL 480: 480 µg/kg/bid) or acamprosate (ACP 32: 32 µg/kg/bid) as monotherapies (FIG. 1-B). However, with an improvement of more than 40% of their alternation as compared to Abeta 25-35 intoxicated mice, compositions of the invention at different dosages (BCL 480, ACP 32 and C8MCT 0.555; BCL 192, ACP 12.8 and C8MCT 1.66) cause a statistically significant prevention of impairment (FIG. 1-C), demonstrating an unexpected effect of the compositions of the invention.

The combination of higher doses of baclofen (BCL 1200: 1200 µg/kg/bid) and acamprosate (ACP 80: 80 µg/kg/bid) confirms the efficiency of this drug combination in improving cognitive performances in diseased animals (FIG. 1-C, diagonally striped bar). The improvement achieved with the use of the mixes BCL 480-ACP 32-C8MCT 0.555 and BCL 192-ACP 12.8-C8MCT 1.66 is of the same extent (i.e., there is no statistically significant difference between the percentages of alternation, bilateral type 3 Student's test, $P>0.05$) than that observed with the BCL 1200-ACP 80 mix, although the doses of baclofen and acamprosate are 2.5 and more than 6 times lower. A statistically significant synergistic effect has been calculated by ANOVA between the compounds of the BCL 480-ACP 32-C8MCT 0.555 mix ($F=3.53$, $P<0.001$) and of the BCL 192-ACP 12.8-C8MCT 1.66 mix ($F=3.11$, $P<0.005$).

The effects of the compositions of the invention have been further confirmed on long-term memory (FIG. 2; A: caprylic triglyceride at three doses; B: baclofen or acamprosate; C: combination of baclofen, acamprosate with/without caprylic triglyceride, combined doses). The results obtained show that the intoxicated animals exhibit impaired behavioral and cognitive performances according to their scores in the step-through latency test, and that compositions of the invention (BCL 480-ACP 32-C8MCT 0.555; BCL 192-ACP 12.8-C8MCT 1.66) induce an unexpected synergistic effect in the reduction of such impairment ($F=3.51$, $P<0.001$).

Memory impairment is an early feature of Alzheimer's disease and symptomatic of neuronal and synaptic damages; these results clearly show that the toxic effect of amyloid peptide on behavioral and cognitive performances (including memory) is significantly prevented by the compositions of the invention.

REFERENCES

1 Crook R, Verkkoniemi A, Perez-Tur J, Mehta N, Baker M, Houlden H, Farrer M, Hutton M, Lincoln S, Hardy J, Gwinn K, Somer M, Paetau A, Kalimo H, Ylikoski R, Poyhonen M, Kucera S & Haltia M (1998) A variant of Alzheimer's disease with spastic paraparesis and unusual plaques due to deletion of exon 9 of presenilin 1. *Nat. Med.* 4, 452-5.

2 Houlden H, Baker M, McGowan E, Lewis P, Hutton M, Crook R, Wood N W, Kumar-Singh S, Geddes J, Swash M, Scaravilli F, Holton J L, Lashley T, Tomita T, Hashimoto T, Verkkoniemi A, Kalimo H, Somer M, Paetau A, Martin J J, Van Broeckhoven C, Golde T, Hardy J, Haltia M & Revesz T (2000) Variant Alzheimer's disease with spastic paraparesis and cotton wool plaques is caused by PS-1 mutations that lead to exceptionally high amyloid-beta concentrations. *Ann. Neurol.* 48, 806-8.

3 Kwok J B, Taddei K, Hallupp M, Fisher C, Brooks W S, Broe G A, Hardy J, Fulham M J, Nicholson G A, Stell R, St George Hyslop P H, Fraser P E, Kakulas B, Clarnette R, Relkin N, Gandy S E, Schofield P R & Martins R N (1997) Two novel (M233T and R278T) presenilin-1 mutations in early-onset Alzheimer's disease pedigrees and preliminary evidence for association of presenilin-1 mutations with a novel phenotype. Neuroreport 8, 1537-42.

4 Verkkoniemi A, Kalimo H, Paetau A, Somer M, Iwatsubo T, Hardy J & Haltia M (2001) Variant Alzheimer disease with spastic paraparesis: neuropathological phenotype. *J. Neuropathol. Exp. Neurol.* 60, 483-92.

5 Citron M (2004) Strategies for disease modification in Alzheimer's disease. *Nat. Rev. Neurosci.* 5, 677-85.

6 Suh Y-H & Checler F (2002) Amyloid precursor protein, presenilins, and alpha-synuclein: molecular pathogenesis and pharmacological applications in Alzheimer's disease. *Pharmacol. Rev.* 54, 469-525.

7 Blacker D, Albert M S, Bassett S S, Go R C, Harrell L E & Folstein M F (1994) Reliability and validity of NINCDS-ADRDA criteria for Alzheimer's disease. The National Institute of Mental Health Genetics Initiative. *Arch. Neurol.* 51, 1198-204.

8 Rossor M N, Fox N C, Freeborough P A & Harvey R J (1996) Clinical features of sporadic and familial Alzheimer's disease. *Neurodegeneration* 5, 393-7.

9 Glenner G G, Wong C W, Quaranta V & Eanes E D (1984) The amyloid deposits in Alzheimer's disease: their nature and pathogenesis. *Appl. Pathol.* 2, 357-69.

10 Ballatore C, Lee V M-Y & Trojanowski J Q (2007) Tau-mediated neurodegeneration in Alzheimer's disease and related disorders. *Nat. Rev. Neurosci.* 8, 663-72.

11 DiLuca M, Bell K F S & Claudio Cuello A (2006) Altered synaptic function in Alzheimer's disease. *Eur. J. Pharmacol.* 545, 11-21.

12 Hardy J A & Higgins G A (1992) Alzheimer's disease: the amyloid cascade hypothesis. *Science* 256, 184-5.

13 Braak H & Braak E (1991) Neuropathological staging of Alzheimer-related changes. *Acta Neuropathol.* 82, 239-59.

14 Golde T E (2005) The Abeta hypothesis: leading us to rationally-designed therapeutic strategies for the treatment or prevention of Alzheimer disease. *Brain Pathol.* 15, 84-7.

15 Hardy J & Selkoe D J (2002) The amyloid hypothesis of Alzheimer's disease: progress and problems on the road to therapeutics. *Science* 297, 353-6.

16 Selkoe D J (2000) The genetics and molecular pathology of Alzheimer's disease: roles of amyloid and the presenilins. *Neurol. Clin.* 18, 903-22.

17 Zlokovic B V (2008) The blood-brain barrier in health and chronic neurodegenerative disorders. *Neuron* 57, 178-201.

18 Budd Haeberlein S L & Lipton S A (2009) Excitotoxicity in neurodegenerative disease. In *Encyclopedia of Neuroscience* (Squire L R, ed.), pp. 77-86. Elsevier.

19 McGleenon B M, Dynan K B & Passmore A P (1999) Acetylcholinesterase inhibitors in Alzheimer's disease. *Br. J. Clin. Pharmacol.* 48, 471-480.

20 Parsons C G, Danysz W & Quack G (1999) Memantine is a clinically well tolerated N-methyl-D-aspartate 21 Gauthier S & Scheltens P (2009) Can we do better in developing new drugs for Alzheimer's disease? Alzheimer's Dement. 5, 489-491.

22 Aliabadi A, Foroumadi A, Mohammadi-Farani A & Garmsiri Mahvar M (2013) Synthesis and Evaluation of Anti-acetylcholinesterase Activity of 2-(2-(4-(2-Oxo-2-phenylethyl)piperazin-1-yl) ethyl)Isoindoline-1,3-dione Derivatives with Potential Anti-Alzheimer Effects. *Iran. J. Basic Med. Sci.* 16, 1049-54.

23 Kaduszkiewicz H & Hoffmann F (2008) Review: cholinesterase inhibitors and memantine consistently but marginally improve symptoms of dementia. *Evid. Based. Ment. Health* 11, 113.

24 Galvin J E (2012) OPTIMIZING DIAGNOSIS AND MANANGEMENT IN MILD-TO-MODERATE ALZHEIMER'S DISEASE. *Neurodegener. Dis. Manag.* 2, 291-304.

25 Lipton S A (2004) Failures and successes of NMDA receptor antagonists: molecular basis for the use of open-channel blockers like memantine in the treatment of acute and chronic neurologic insults. *NeuroRx* 1, 101-10.

26 Lipton S A (2006) Paradigm shift in neuroprotection by NMDA receptor blockade: memantine and beyond. *Nat. Rev. Drug Discov.* 5, 160-70.

27 Magnaghi V, Ballabio M, Consoli A, Lambert J J, Roglio I & Melcangi R C (2006) GABA Receptor-Mediated Effects in the Peripheral Nervous System: A Cross-Interaction With Neuroactive Steroids. *J. Mol. Neurosci.* 28, 89-102.

28 Struble R G, Ala T, Patrylo P R, Brewer G J & Yan X-X (2010) Is brain amyloid production a cause or a result of dementia of the Alzheimer's type? *J. Alzheimers. Dis.* 22, 393-9.

29 Cunnane S, Nugent S, Roy M, Courchesne-Loyer A, Croteau E, Tremblay S, Castellano A, Pifferi F, Bocti C, Paquet N, Begdouri H, Bentourkia M, Turcotte E, Allard M, Barberger-Gateau P, Fulop T & Rapoport S I (2011) Brain fuel metabolism, aging, and Alzheimer's disease. *Nutrition* 27, 3-20.

30 Uemura E & Greenlee H W (2001) Amyloid beta-peptide inhibits neuronal glucose uptake by preventing exocytosis. *Exp. Neurol.* 170, 270-6.

31 Henderson S T, Vogel J L, Barr L J, Garvin F, Jones J J & Costantini L C (2009) Study of the ketogenic agent AC-1202 in mild to moderate Alzheimer's disease: a randomized, double-blind, placebo-controlled, multi-center trial. *Nutr. Metab.* (Loud). 6, 31.

32 Association A (2011) Alzheimer's association, Alternative treatments. http://www.alz.org/alzheimers_disease_alternative_treatments.asp.

33 Stella V J (2007) Prodrugs: challenges and rewards. (A. Press and Springer, eds.) Springer Singapore Pte. Limited, New York.

34 Wermuth C G (2011) *The Practice of Medicinal Chemistry*. Elsevier Science.

35 Pezron I, Mitra A K, Duvvuri S & Tirucherai G S (2002) Prodrug strategies in nasal drug delivery. *Expert Opin. Ther. Pat.* 12, 331-340.

36 Stella V J (2004) Prodrugs as therapeutics. *Expert Opin. Ther. Pat.* 14, 277-280.

37 Stella V J & Nti-Addae K W (2007) Prodrug strategies to overcome poor water solubility. *Adv. Drug Deliv. Rev.* 59, 677-94.

38 Beaumont K, Webster R, Gardner I & Dack K (2003) Design of ester prodrugs to enhance oral absorption of poorly permeable compounds: challenges to the discovery scientist. *Curr. Drug Metab.* 4, 461-85.

39 Higuchi T & Stella V J (1975) *Pro-drugs as Novel Drug Delivery System*, ACS Sympos American Chemical Society, Washington, D.C.

40 Roche E B (1977) *Design of biopharmaceutical properties through prodrugs and analogs: a symposium*, The Academy of Pharmaceutical Sciences, Washington, D C.

41 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.

42 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.

43 Wishart D S, Knox C, Guo A C, Cheng D, Shrivastava S, Tzur D, Gautam B & Hassanali M (2008) DrugBank: a knowledgebase for drugs, drug actions and drug targets. *Nucleic Acids Res.* 36, D901-6.

44 Leach A R & Gillet V J *An Introduction to Chemoinformatics* (Springer-Verlag New York, Inc., ed.).

45 Rahman S A, Bashton M, Holliday G L, Schrader R & Thornton J M (2009) Small Molecule Subgraph Detector (SMSD) toolkit. *J. Cheminform.* 1, 12.

46 Stahl H & Wermuth C G (2011) *Pharmaceutical salts: Properties, selection, and use*, 2nd ed. (Wiley).

47 Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.

48 Chou T-C (2006) Theoretical basis, experimental design, and computerized simulation of synergism and antagonism in drug combination studies. *Pharmacol. Rev.* 58, 621-81.

49 Grabovsky Y & Tallarida R J (2004) Isobolographic analysis for combinations of a full and partial agonist: curved isoboles. *J. Pharmacol. Exp. Ther.* 310, 981-6.

50 Berenbaum M C (1977) Synergy, additivism and antagonism in immunosuppression. A critical review. *Clin. Exp. Immunol.* 28, 1-18.

51 Slinker B K (1998) The Statistics of Synergism. *J. Mol. Cell. Cardiol.* 30, 723-731.

52 Gennaro A R (2000) *Remington: The Science and Practice of Pharmacy*, 20th ed. Lippincott Williams & Wilkins.

53 Swarbrick J & Boylan J C (eds.) *Encyclopedia of Pharmaceutical Technology* Marcel Dekker, New York.

54 Meunier J, Ieni J & Maurice T (2006) The anti-amnesic and neuroprotective effects of donepezil against amyloid beta25-35 peptide-induced toxicity in mice involve an interaction with the sigma1 receptor. *Br. J. Pharmacol.* 149, 998-1012.

The invention claimed is:

1. A composition comprising baclofen and acamprosate, or pharmaceutically acceptable salts, hydrates, isomers, racemates, enantiomerically pure compositions or conjugates thereof; and a medium chain triglyceride of the formula:

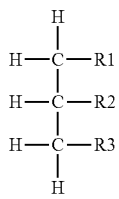

wherein R1, R2 and R3 are each the same medium chain fatty acid consisting of caprylic acid (C8).

2. The composition according to claim 1, wherein the medium chain triglyceride is from coconut oil, palm kernel oil, or *Cuphea* genus seed oil, or extract(s) thereof.

3. The composition according to claim 1, wherein the medium chain triglyceride is from *Cuphea pulcherrima* seed oil, or an extract thereof.

4. The composition according to claim 1, wherein said composition comprises the following combination of compounds:
baclofen and acamprosate and caprylic triglyceride,
or pharmaceutically acceptable salts, hydrate, isomers, racemates, enantiomerically pure composition, or conjugates thereof.

5. The composition according to claim 1, which further comprises a pharmaceutically acceptable carrier or excipient.

6. A method of treating a neurological disorder in a subject in need thereof, the method comprising administering to said subject an effective amount of a composition according to claim 1.

7. The method according to claim 6, wherein the neurological disorder is selected from Alzheimer's disease, an Alzheimer's disease related disorder, frontotemporal dementia, amyotrophic lateral sclerosis, multiple sclerosis, epilepsy, spinal cord injury, a peripheral neuropathy, alcoholism or alcohol withdrawal, traumatic brain injury or a brain ischemic event, Parkinson's disease, Lewy body dementia, Huntington's disease, a neurological manifestation of drug abuse, and drug abuse withdrawal.

8. The method according to claim 6, wherein the compounds are formulated separately.

9. The method according to claim 6, wherein the compounds are administered together, separately or sequentially.

10. The method according to claim 6, wherein compounds are administered repeatedly to the subject.

11. The method according to claim 6, wherein the ratio acamprosate/baclofen (w/w) is comprised between 0.05 and 1000.

12. The method according to claim 6, wherein the dose of baclofen is less than 100 mg/day.

13. The method according to claim 6, wherein the dose of acamprosate is less than 100 mg/day.

14. The method according to claim 6, wherein acamprosate is administered in the form of a calcium salt of acamprosate.

15. The method according to claim 6, wherein said compounds are formulated together as an admixture.

* * * * *